United States Patent [19]
Crosby et al.

[11] 3,952,058
[45] Apr. 20, 1976

[54] SWEETENER

[75] Inventors: Guy A. Crosby, Palo Alto; Patrick M. Saffron, Los Gatos, both of Calif.

[73] Assignee: Dynapol, Palo Alto, Calif.

[22] Filed: Oct. 16, 1974

[21] Appl. No.: 509,999

Related U.S. Application Data

[62] Division of Ser. No. 442,482, Feb. 14, 1974, Pat. No. 3,876,814.

[52] U.S. Cl. .............................. 260/575; 260/471 R; 260/473 R; 426/548
[51] Int. Cl.² .................. C07C 93/14; C07C 91/40
[58] Field of Search ...................... 260/575; 426/217

[56] References Cited
UNITED STATES PATENTS

| | | | |
|---|---|---|---|
| 2,278,996 | 4/1942 | Klein | 260/575 |
| 3,520,930 | 7/1970 | Clark et al. | 260/575 |
| 3,845,225 | 10/1974 | Crosby et al. | 260/575 |

OTHER PUBLICATIONS

Finar, Organic Chemistry, Vol. I, Longmans, London, 1963, p. 191.

Wagner et al., Synthetic Organic Chemistry, John Wiley & Sons, N.Y., N.Y., 1953, pp. 155, 226, 567, 654, 678.

Blanksma et al., Rec. Trav. Chim., Vol. 59 (1940), pp. 629–632.

*Primary Examiner*—Arthur P. Demers
*Attorney, Agent, or Firm*—William H. Benz

[57] ABSTRACT

The use of 3-amino-4-n-propoxybenzyl alcohol as a nonnutritive sweetener for foods, beverages and the like is disclosed.

1 Claim, No Drawings

SWEETENER

This is a division of application Ser. No. 442,482, filed Feb. 14, 1974, and now U.S. Pat. No. 3,876,814, issued Apr. 8, 1975.

BACKGROUND OF THE INVENTION

1. Field of the Invention

This invention relates to a process for nonnutritive sweetening and the sweet products of the process.

2. The Prior Art

Nonnutritive, nonsugar sweeteners, commonly known as "artificial sweeteners", have been used for years to eliminate the caloric intake associated with sugar or because of medical conditions such as diabetes.

Possibly because of the major commercial market these products represent or possibly because the nonnutritive sweeteners proposed heretofore have all posed taste, toxicity, or stability problems, there has been a great effort devoted to researching and developing improved sweetener materials. Ideally, a synthetic sweetener would in taste and stability emulate sucrose, the most commonly employed natural sugar sweetener.

STATEMENT OF THE INVENTION

We have now discovered that 3-amino-4-n-propoxybenzyl alcohol possesses a very acceptable sweet taste. When admixed with a foodstuff or like edible materials in an effective amount, it imparts a sweet flavor to the foodstuff.

DETAILED DESCRIPTION OF THE INVENTION

In accordance with the present invention, foodstuffs and other edible substances are given a sweet flavor by having 3-amino-4-n-propoxybenzyl alcohol admixed therewith.

The propoxybenzyl alcohol used in this invention has as its structural formula

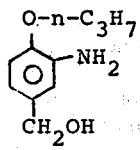

This compound may be prepared by the five-step process of
1. Esterifying 3-nitro-4-hydroxybenzoic acid to yield a first ester product;
2. n-propoxylating the 4 hydroxy group of the first ester product to yield 3-nitro-4-propoxybenzoic acid ester;
3. reducing the 3-nitro group of the 3-nitro-4-n-propoxybenzoic acid ester in acetic acid to an acetamido group;
4. hydrolyzing the acetamido group and the 1-benzoic acid ester functionality to yield 3-amino-4-n-propoxybenzoic acid; and
5. reducing the benzoic acid product of step 4 to the corresponding 3-amino-4-n-propoxybenzyl alcohol.

This preparative scheme is described in more detail in the Examples which follow. Other preparative routes to the desired benzyl alcohol product may be taken as well.

In use, the benzyl alcohol sweetener of this invention is admixed with foodstuffs and the like in an effective amount. The term "effective amount" as used herein denotes an amount of sweetener satisfactory to produce a desired degree of sweetness. Generally, the amount of sweetener employed will range between about 0.01% by weight (basis edible substance) and about 15% by weight (basis edible substance). Preferably, from about 0.1 to about 10% by weight (basis edible substance) of sweetener is employed. It should be recognized, however, that if a desired degree of sweetness is only achieved by using amounts of sweetener falling outside of these ranges (either larger or smaller) such usage levels would still fall within the "effective amount" range contemplated by this invention.

The sweetener of this invention finds application in the wide range of edible substances generally, primarily with foodstuffs such as candies, confections and processed foods, and beverages such as beer and soft drinks. It is also well suited for imparting a sweet flavor to other edible substances such as medicines, toothpaste, adhesives for stamps and envelopes, animal feeds and baits, and the like. These examples are given solely for illustration and it is not wished to limit the scope of this invention to sweetening any particular type or types of edible materials. As a general rule, the present sweetener may be used in any application where a sweet taste is desired. The present sweetener may be used alone or in combination with other sweeteners, nutritive or nonnutritive. Also, if desired, binders or diluents may be added to the sweetener. This is not usually necessary, however, as the sweetener is a solid having excellent handling properties. This makes admixing the sweetener with an edible substance a simple conventional operation. The sweetener may be mixed with the edible substance as a solid or as a solution, if desired.

The invention will be further described by the following Examples. These Examples are provided to illustrate the invention and are not to be construed as limiting the scope of the invention.

EXAMPLE 1

Preparation of 3-amino-4-n-propoxybenzyl alcohol

Ia. Esterification of 3-nitro-4-hydroxybenzoic acid:

Commercial 3-nitro-4-hydroxybenzoic acid (Sapon Labs) was esterified with methanol. First a mixture of the acid was formed with 38.4 g of reagent grade methanol, 100 ml of 1,2-dichloroethane and 1.5 ml of concentrated sulfuric acid. The mixture was stirred at reflux temperature for 25 hours. A sample of the reaction mixture was taken and analyzed by a thin layer chromatography technique (direct spotting using 2 parts volume acetic acid/98 parts ethyl acetate as eluent) and found to contain only a small amount of the starting acid. The ester product was recovered by diluting with dichloromethane, washing with water, 5% sodium bicarbonate and water again, drying with magnesium sulfate and Norit and evaporating to yield 32.7 g of yellow solid product, methyl 3-nitro-4-hydroxybenzoate, mp 72°–73°.

b. n-propoxylating the methyl 3-nitro-4-hydroxybenzoate:

A 10.2 g portion of the product of step (a) was mixed with 17.6 g of potassium carbonate and 700 ml of dried acetone and refluxed with vigorous stirring for one hour. Then 106 g of n-propyl iodide was added and the mixture was stirred and refluxed for an additional 23 hours. The reaction mixture was filtered and the solvent was removed under reduced pressure. The residue was dissolved in diethyl ether and the solution then washed, first with 3% sodium hydroxide and then with water. The solution was dried with magnesium sulfate and stripped of solvent to yield 12.0 g of a pale yellow material which upon analysis was shown to be methyl 3-nitro-4-n-propoxybenzoate, mp 62°–63°.

c. Converting the 3-nitro group to an acetamido group:

A 4.8 g portion of the product of step (b) was dissolved in 300 ml of glacial acetic acid. 4.5 g of hydrogen-reduced iron powder was then added and the mixture was refluxed for 21 hours. The mixture was filtered and the solvent was stripped under reduced pressure. The solid residue recovered was mixed with 10% sodium chloride solution and extracted twice with diethyl ether. The ether extract was dried and evaporated to yield 4.4 g of a white solid which, upon analysis, was shown to be methyl 3-acetamino-4-n-propoxybenzoate, mp 94°–95°.

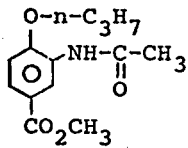

Thus the 3-nitro group had been reduced initially to an amine and converted further into an acetamido group by the action of acetic acid and heat.

d. Hydrolyzing:

A 3.4 g portion of the product of step (c) was added to 120 ml of 3 N hydrochloric acid. The mixture was refluxed for 70 minutes and cooled in an ice bath for five hours. A white precipitate formed and was collected and dried to yield 3.0 g of a material determined to be 3-amino-4-n-propoxy benzoic acid hydrochloride, mp 233°–236°.

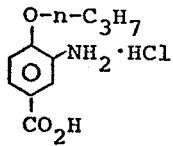

This product was then dissolved in 100 ml of water and titrated to a pH curve inflection point at 3.2 with 0.5 N KOH. A white precipitate formed when the solution was chilled. This precipitate was collected and dried and found to be 3.2 g of 3-amino-4-n-propoxybenzoic acid, mp 121°–122°.

e. Reducing the benzoic acid:

A 195 mg portion of the product of step (d) was added to 3.0 ml of a 70% solution in benzene of sodium bis-(2-methoxy-ethoxy)aluminum hydride (Research) Organic/Inorganic Chem. Corp.). The mixture was stirred under argon for 3 hours at 80° and then slowly diluted with 3N hydrochloric acid and then brought to pH 8 with 5% potassium hydroxide. The mixture was extracted twice with diethyl ether (sodium chloride being added to salt out the product) and the extracts were then dried over magnesium sulfate and Norit and evaporated to yield a pale solid product, which upon removal of the ether under reduced pressure, was found to weigh 146 mg. Analysis of this product showed it to be 3-amino-4-n-propoxybenzyl alcohol. A sample crystallized from water melted at 94°–95°.

II. A saturated aqueous solution of the product of part I was prepared. A group of volunteers tasted this solution and all found it to have a pleasing sweet taste.

EXAMPLE 2

The preparation of part I of Example 1 was repeated with two major changes. The amounts of material employed were increased by a factor of about 10. The reduction in step (e) was carried out differently. To a solution of 1.1 g of lithium aluminum hydride (Alfa Inorganics-Ventron) in 50 ml of scrupulously dried tetrahydrofuran was added dropwise with stirring 2 g of 3-amino-4-n-propoxybenzoic acid in 100 ml of scrupulously dried tetrahydrofuran. The mixture was refluxed for 20 minutes, cooled, diluted with 1 ml of 15% potassium hydroxide and 3 ml of water. Then 150 ml of diethyl ether was added to extract the product. The ether extract was separated, dried and evaporated to yield 1.6 g of the 3-amino-4-n-propoxybenzyl alcohol product, mp 94°–95°.

When this material is added to gelatin in combination with a fruit flavor and color to yield a dessert product, the amino-4-n-propoxybenzyl alcohol imparts a sweet flavor to the product. Likewise, when 3-amino-4-n-propoxybenzyl alcohol is added to cola beverages and to chewing gum it imparts desired sweet flavors thereto.

We claim as our invention:

1. The compound 3-amino-4-n-propoxybenzyl alcohol.

* * * * *